(12) United States Patent
Karandikar et al.

(10) Patent No.: US 8,652,531 B2
(45) Date of Patent: Feb. 18, 2014

(54) INDICATOR FOR OXYGEN GENERATION

(75) Inventors: Bhalchandra M. Karandikar, Beaverton, OR (US); Carin J. Berg, Portland, OR (US); Sophie Truc Lam, Beaverton, OR (US); Sunita J. Macwana, Tigard, OR (US); Zhongju Liu Zhao, Sherwood, OR (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 18 days.

(21) Appl. No.: 13/555,332

(22) Filed: Jul. 23, 2012

(65) Prior Publication Data
US 2013/0028983 A1    Jan. 31, 2013

Related U.S. Application Data

(60) Provisional application No. 61/513,137, filed on Jul. 29, 2011.

(51) Int. Cl.
*A01N 39/00*    (2006.01)

(52) U.S. Cl.
USPC .......................................... 424/616; 424/639

(58) Field of Classification Search
None
See application file for complete search history.

(56) References Cited

U.S. PATENT DOCUMENTS

| | | |
|---|---|---|
| 4,969,881 A | 11/1990 | Viesturs |
| 5,792,090 A | 8/1998 | Ladin |
| 6,293,433 B1 | 9/2001 | Joulia |
| 6,322,798 B1 | 11/2001 | Candau et al. |
| 6,333,093 B1 | 12/2001 | Burrell et al. |
| 6,458,109 B1 | 10/2002 | Henley et al. |
| 6,767,342 B1 | 7/2004 | Cantwell |
| 7,160,553 B2 | 1/2007 | Gibbins et al. |
| 2003/0232114 A1 | 12/2003 | Dekleva |
| 2004/0086453 A1 | 5/2004 | Howes |
| 2005/0232953 A1 | 10/2005 | Barnikol et al. |
| 2006/0030900 A1 | 2/2006 | Eckert |
| 2007/0031348 A1 | 2/2007 | Staeb et al. |
| 2007/0166339 A1 | 7/2007 | Gupta |
| 2009/0202617 A1 | 8/2009 | Ward et al. |
| 2009/0258841 A1 | 10/2009 | Murphy et al. |
| 2010/0035798 A1 | 2/2010 | Sen et al. |
| 2010/0112087 A1 | 5/2010 | Harrison et al. |
| 2010/0255162 A1 | 10/2010 | Becraft et al. |
| 2011/0015565 A1 | 1/2011 | Hursey |

FOREIGN PATENT DOCUMENTS

| WO | WO 94/21323 A1 | 9/1994 |
|---|---|---|
| WO | WO 02/060458 A2 | 8/2002 |
| WO | WO 2008/131070 A1 | 10/2008 |
| WO | WO 2009/031788 A1 | 3/2009 |
| WO | WO 2009/127058 A1 | 10/2009 |

OTHER PUBLICATIONS

Wekesa, Moses et al., Mechanism of hydrogen peroxide decomposition by manganese dioxide, Tappi Journal, vol. 2, No. 9, Sep. 2003, pp. 23-26.*
Co-pending U.S. Appl. No. 13/555,336, filed Jul. 23, 2012, by Karandikar et al. for "Two Part Oxygen Generating System".
Li, Yali et al., "Gold Nanoparticles Mediate the Assembly of Manganese Dioxide Nanoparticles for H2O2 Amperometric Sensing," Electrochimica Acta, Elsevier Science Publishers, vol. 55, No. 18, Jul. 15, 2010, pp. 5123-5128.
Li, Jun et al., "Nickel Foam-Based Manganese Dioxide-Carbon Nanotube Composite Electrodes for Electrochemical Supercapacitors," Journal of Power Sources, Elsevier, vol. 185, No. 2, Dec. 1, 2008, pp. 1569-1574.
Luo, Yonglan, "Preparation of MnO2 Nanoparticles by Directly Mixing Potassium Permanganate and Polyelectrolyte Aqueous Solutions," Materials Letters, vol. 61, No. 8-9, Mar. 12, 2007, pp. 1893-1895.
Nam, Ho-Seong et al., "Supercapacitive Properties of a Nanowire-Structured MnO2 Electrode in the Gel Electrolyte Containing Silica," Electrochimica Acta, Elsevier Science Publishers, vol. 55, No. 25, Oct. 30, 2010, pp. 7443-7446.
Wang, Shufen et al., "One-step Synthesis of Manganese Dioxide/Polystyrene Nanocomposite Foams via High Internal Phase Emulsion and Study of Their Catalytic Activity," Colloid and Polymer Science, vol. 288, No. 9, May 16, 2010 pp. 1031-1039.
Xu, Mao-Wen et al., "Mesoporous Amorphous MnO2 as Electrode Material for Supercapacitor," Journal of Solid State Electrochemistry, vol. 11, No. 8, Jan. 10, 2007, pp. 1101-1107.
Yu, Peng et al., "Preparation and Pseudo-Capacitance of Birnessite-Type MnO2 Nanostructures via Microwave-Assisted Emulsion Method," Materials Chemistry and Physics, Elsevier, vol. 118, No. 2-3, Dec. 15, 2009, pp. 303-307.

* cited by examiner

*Primary Examiner* — Lezah Roberts
*Assistant Examiner* — Nannette Holloman
(74) *Attorney, Agent, or Firm* — James B. Robinson (57) ABSTRACT

There is provided on-demand, oxygen generating topical compositions having a built-in indicator specifically to indicate a color change upon the complete mixing of the oxygen precursor and catalyst. The first part of the composition contains a carrier and manganese dioxide (MnO2) nanoparticles. The second part of the composition comprises the oxygen precursor; hydrogen peroxide. When the two parts, one with manganese dioxide nanoparticles and exhibiting a characteristic color, (e.g. yellow brown) and the second part with hydrogen peroxide are mixed together, the color imparted by the manganese dioxide nanoparticles essentially disappears and the final composition (enriched with oxygen) either appears colorless or takes on the original color of the catalyst. Thus, the manganese dioxide catalyst nanoparticles themselves serve as the colorimetric indicator of peroxide decomposition to oxygen, precluding the need for an external colorant. Manganese dioxide particles that are not nanoparticles fail to exhibit this color changing phenomenon.

3 Claims, 6 Drawing Sheets

INDICATOR FOR OXYGEN GENERATION

This application claims the benefit of priority from U.S. Provisional Application No. 61/513,137 filed on Jul. 29, 2011, the contents of which are incorporated herein by reference.

BACKGROUND

The present disclosure relates to an indicator of oxygen generation in cosmetic formulations.

Oxygen is essential to sustaining life. Marine life utilize oxygen in dissolved form whereas land based species including humans utilize gaseous oxygen. The lack of oxygen or hypoxia is commonly experienced by people in their extremities (e.g. feet) as they get older due to poor blood circulation as well as by those with conditions such as diabetes. Studies have also shown below normal, low oxygen tension in the skins of older people. This often leads to poor skin health and an excessive presence of visible conditions such as wrinkles, dryness and lower skin elasticity. Over the years, cosmetic manufacturers have introduced skin formulations with a large variety of ingredients such as emollients, exfoliators, moisturizers etc., to retard these age related effects and improve and maintain skin health.

While some cosmetic formulators have focused on maintaining moisture, natural oils and providing nutrients to the skin, others have taken a different approach. This approach has looked at the role of oxygen from the medical point of view e.g. in treating of the compromised skin (wounds, inflammation and trauma) and more recently, intact skin. For example, Ladizinsky patented an oxygen generating wound dressing (U.S. Pat. No. 5,792,090), that is unfortunately somewhat difficult to manufacture. More recently, Gibbins et al. patented a method of making an oxygen generating foam dressing based on a polyacrylate polymer (U.S. Pat. No. 7,160,553). While the method of making an oxygen generating foam dressing is straightforward, the dressing itself suffers from a few drawbacks. For instance, the shelf life of the dressing is insufficient because oxygen from the dressing diffuses out of the foam cells over time. An alternative to the foam dressing in the form of an on-demand oxygen generating topical composition was proposed to overcome the limitation of the short shelf life (Ladizinsky US2009/0074880).

Unfortunately the catalytic decomposition of hydrogen peroxide to oxygen is quite rapid and the end user of such a composition has no way of observing if the mixing of the two parts has been thorough. An indicator system that could undergo some kind of visual change would be advantageous for broad acceptance of the product.

There is a need for an indicator system for ensuring thorough mixing of the two parts of the topical composition before or during its application to the skin. Indicator systems based on dyes and colorants have been used in variety of other applications, e.g. an indicator system to show proper cooling of a beverage as indicated by a color change upon reaching a certain temperature. An indicator system based on dye or pigment for an oxygen generating topical composition would require the use of a coloring ingredient whose by-product of discoloration may not suitable for the skin. Additionally, its color changing property could be unevenly affected by a variety of ingredients that are typically present in cosmetic formulations, rendering the product performance unpredictable.

SUMMARY

The problem discussed above has found a solution to a large degree in the present disclosure, which describes the use of manganese dioxide nanoparticles which, when added into the catalyst carrying part of the topical composition, can serve as an indicator. Manganese dioxide particles that are not nanoparticles fail to exhibit this color changing phenomenon. The proposed composition is a dual part system wherein one part contains a manganese dioxide ($MnO_2$) catalyst and the second part contains a precursor of oxygen (hydrogen peroxide or $H_2O_2$). When needed, the two parts (in equal proportion) are brought together to effect the decomposition of hydrogen peroxide to generate oxygen.

The first part of the composition contains a carrier and manganese dioxide nanoparticles. Manganese dioxide nanoparticles with an average size in 10-100 nm range have an absorption maximum between 330-370 nm. In aqueous or non-aqueous solutions these particles impart a yellow-brown color due to their characteristic plasmon resonance band. Other nanoparticle sizes are expected to similarly impart a discernable color. The second part of the composition comprises the oxygen precursor; hydrogen peroxide. When the two parts, one with manganese dioxide nanoparticles and exhibiting a characteristic color, (e.g. yellow brown) and the second part with hydrogen peroxide are mixed together, the color imparted by the manganese dioxide nanoparticles fades and may essentially disappear and the final composition (enriched with oxygen) either appears colorless or takes on the original color of the catalyst comprising part prior to addition of manganese dioxide.

The gradual loss of the color to colorless (or to the appearance of the original color before the addition of manganese dioxide nanoparticles) is accompanied by the corresponding hydrogen peroxide decomposition and liberation of oxygen. Thus, the manganese dioxide catalyst nanoparticles themselves serve as the colorimetric indicator of peroxide decomposition to oxygen, precluding the need for an external colorant.

Disclosed are the on-demand oxygen generating topical compositions having a built-in indicator specifically to indicate a color change (usually from colored to colorless) upon the complete mixing of the oxygen precursor and catalyst. Also disclosed are oxygen generating compositions where upon mixing the two parts, the original color of the manganese dioxide containing composition reappears. For example, if the original color of the manganese dioxide containing part (prior to manganese dioxide addition) is blue, upon addition of manganese dioxide it changes to greenish blue to teal color. When this part is mixed with the hydrogen peroxide containing part, the teal color changes back to blue.

The methods of making the compositions and the methods of using the compositions are disclosed where the maximum amount of hydrogen peroxide is 3% or less of its respective constituent composition. More specifically, the methods of using the compositions in the treatment of intact skin (both non-compromised and compromised) and not the breached skin are disclosed. By compromised skin, it is meant that the skin may have inflammation or trauma, may be lacking healthy oxygen tension levels but that the stratum corneum is generally intact. By non-compromised skin, it is meant that skin is generally healthy but may still be showing signs of usual age related wear and tear including less elasticity, less moisture levels etc.

The disclosed topical compositions having a catalyst containing part and an oxygen precursor part may be either aqueous, non-aqueous or a mixture of the two e.g. emulsions. Both oil in water (o/w) or water in oil (w/o) compositions are encompassed by the present disclosure. To impart additional cosmetically desirable properties, the component compositions (with catalyst and oxygen precursor) may contain other ingredients such as natural or synthetic polymers, moisturizers, humectants, viscosity modifiers, emollients, texture enhancers, UV blocking agents, colorants, pigments, ceramics (fumed silica, titanium dioxide, natural and synthetic clays), antioxidants, fragrances etc.

DETAILED DESCRIPTION

Reference will now be made in detail to one or more embodiments of the invention, examples of the invention, examples of which are illustrated in the drawings. Each example and embodiment is provided by way of explanation of the invention, and is not meant as a limitation of the invention. For example, features illustrated or described as part of one embodiment may be used with another embodiment to yield still a further embodiment. It is intended that the invention include these and other modifications and variations as coming within the scope and spirit of the invention.

The application of oxygen to the skin can help to alleviate a number of problems brought on by ageing such as poor skin health and an excessive presence of visible conditions such as wrinkles, dryness and lower skin elasticity. Oxygen applied to the skin can help to retard these age related effects and improve and maintain skin health.

Applying oxygen to the skin topically through the application of a liquid or foam composition is a convenient, easy and quick method of delivering the desired benefits discussed above. A two part formulation as disclosed herein helps to ensure that the oxygen is available for use and has not been lost during storage. Delivering oxygen in the form of a peroxide helps ensure the oxygen remains present until it is needed, since oxygen is a fugitive substance that is highly reactive. Catalyzing the peroxide with manganese dioxide to produce oxygen on-demand allows the consumer to choose when the oxygen is delivered. It is important with two part systems, however, that the two components be thoroughly mixed to ensure that the maximum amount of oxygen is released to deliver the maximum benefit. There is currently no system of delivering on-demand oxygen with an indicator that will show that the components are thoroughly mixed so the user cannot tell that the proper application procedure has been followed. The nanoparticle sized particle delivery disclosed herein allows the user to visually discern that thorough mixing has been achieved and that the maximum amount of oxygen has been liberated from the mixture.

Nanoparticle sized manganese dioxide means particles in the range of from 1 to 1000 nanometers, more desirably from 5 to 500 nanometers and still more desirably from 50 to about 300 nanometers. Base solutions containing manganese dioxide nanoparticles have a tan or yellow brown color. The base solution may be a liquid, gel, foam or emulsion of oil in water or water in oil. Examples of base solutions are given below.

Once the base solution containing the nanoparticle manganese dioxide has been made, it may be stored for later use without deterioration of the manganese dioxide. Likewise the second component, the hydrogen peroxide, may be stored separately without deterioration under the proper conditions. Once it is desired to liberate the oxygen from the hydrogen peroxide and treat the skin, the two components should be thoroughly mixed to release the maximum amount of oxygen. It has been found that the addition of the hydrogen peroxide to the nanoparticle manganese dioxide solution results in a change of color from the characteristic manganese dioxide color to the color of the base solution prior to addition of the manganese dioxide. This change does not occur with larger sized manganese dioxide particles and allows the user to clearly see that the mixing has been properly done.

The concentration of manganese dioxide in the base solution may be between 500 and 10000 ppm, more desirably between about 900 and 5000 ppm, and the concentration of hydrogen peroxide generally from a positive amount to about 3 weight percent.

Example 1

Production of Manganese Dioxide Nanoparticles Solutions

The manganese dioxide nanoparticles solutions described below were perceived as transparent (hence the use of the term solution rather than suspension). This transparency is because the manganese dioxide particles are of nano-size and smaller than the wavelength of light. This means the light rays are not scattered and pass straight through the manganese dioxide nanoparticles solutions.

A. 900 ppm Manganese Dioxide Nanoparticles in Solution 0.374 gram of Poly-Allylamine Hydrochloride (PAH, 15,000 Mw, 93.5 g/mol, Aldrich) was dissolved in 50 mL of de-ionized (Di) water to prepare 0.08M solution. 0.158 gram of Potassium Permanganate (158.03 g/mol, Riedel-de-Haen) was dissolved in 50 mL of Di water to give 0.02M solution. Both solutions were mixed in a glass beaker (250 mL capacity) at room temperature with a magnetic stirrer. Upon mixing, the color of the mixed solutions changed from dark red to dark brown in 2-3 minutes, indicating the reduction reaction ($KMnO_4$ to manganese dioxide) took place. The final reacted mixed solution, equivalently termed manganese dioxide nanoparticles solution, had approximately 900 ppm manganese dioxide.

B. 4500 ppm Manganese Dioxide Nanoparticles in Solution

The amounts of PAH and potassium permanganate were increased 5-fold, i.e. from 0.374 to 1.87 gm PAH and 0.158 to 0.79 gm $KMnO_4$, but keeping the amount of DI water the same, i.e. 50 ml. As a result, the molarities increased from 0.08M to 0.4M for the PAH and from 0.02M to 0.1M for $KMnO_4$. The ppm of manganese dioxide increased five fold; from 900 to 4500 ppm. This solution was prepared to yield samples for certain analytical testing. This solution was filtered via a dialyzer in order to remove low molecular weight impurities i.e. K, Cl ions from the manganese dioxide nanoparticles solution. After such filtering, the solution was diluted with water to yield a manganese dioxide nanoparticle concentration of ~2300 ppm.

The presence of manganese dioxide in the final reacted mixed solutions was concluded from the results of UV-VIS spectrum analysis on the 900 ppm manganese dioxide in solution and x-ray photoelectron spectroscopy (XPS) Surface analysis and transmission electron microscopy (TEM) analysis on the filtered 4500 ppm manganese dioxide in solution. The UV-VIS spectrum of the final reacted mixed solutions was recorded and showed a peak at 350 nm, which indicates the presence of manganese dioxide. XPS Surface analysis was performed on a sample of the final reacted mixed solutions by XPS using a Fisons M-Probe spectrometer equipped with monochromatic Al K-rays. Atomic sensitivity factors, supplied with the Fisons M-Probe spectrometer, were used to establish the relative atomic concentration of the elements detected by the spectrometer. The sample for XPS analysis was dried on an aluminum coated glass slide and analyzed at seven different locations across the dried residue. No aluminum was detected for any of the analyzed regions signifying that the sample thickness was greater than the analysis depth of the technique (~10 nm). The elemental analysis results from the XPS analysis are shown in Table I.

TABLE 2

| XPS Curve Fit Results for manganese | | | | | |
|---|---|---|---|---|---|
| High Resolution Scans | Mn 2p3/2 | Mn 2p1/2 | Delta | Mn 2p3/2 | Mn 2p1/2 |
| Analysis # 1 | 641.9 | 653.6 | 11.79 | 63.3 | 36.7 |
| Analysis # 2 | 641.8 | 653.6 | 11.78 | 71.8 | 28.2 |
| Analysis # 3 | 641.5 | 653.3 | 11.81 | 73.2 | 26.8 |
| Analysis # 4 | 642.2 | 654.1 | 11.89 | 74.1 | 25.9 |
| Analysis # 5 | 641.9 | 653.7 | 11.80 | 66.7 | 33.3 |
| Analysis # 6 | 641.8 | 653.6 | 11.78 | 68.5 | 31.5 |
| Analysis # 7 | 641.8 | 653.5 | 11.70 | 68.4 | 31.6 |
| Average | 641.8 | 653.6 | 11.79 | 69.4 | 30.6 |
| Std Dev | 0.2 | 0.2 | 0.1 | 3.8 | 3.8 |
| Theory - manganese dioxide | 641.9-642.2 | | 11.7 | 66.0 | 33.0 |

Binding Energy Reference is Carbon 1s @ 284.6 eV

Transmission electron microscopy (TEM) measurements showed the nanoparticles to be spherical in shape with an average diameter of individual nanoparticles of ~100 nm. (Note: from a reference that described production of manganese dioxide particles via identical experimental conditions reported an average diameter of ~10 nm.) The TEM results gave an average particle size of roughly 103 nm with particle size data listed in Table 3 and graphed in FIG. 2 with fre-

TABLE I

| XPS Analysis of manganese dioxide Nanoparticles on Al Slide | | | | | | | | | |
|---|---|---|---|---|---|---|---|---|---|
| | Atomic Percent | | | | | | | | N |
| | C | N | O | Si | Cl | Mn | Atomic Ratios | | B.E. |
| | 1s | 1s | 1s | 2p | 2p | 2p | N/Cl | N/Mn | Cl/Mn | (eV) |
| Analysis #1 | 83.1 | 3.8 | 8.3 | 1.1 | 2.6 | 1.2 | 1.45 | 3.27 | 2.25 | 400.60 |
| Analysis #2 | 81.1 | 4.5 | 10.0 | 0.4 | 2.7 | 1.4 | 1.69 | 3.33 | 1.97 | 400.87 |
| Analysis #3 | 78.9 | 6.3 | 8.7 | 0.0 | 4.2 | 1.9 | 1.51 | 3.25 | 2.15 | 400.09 |
| Analysis #4 | 83.5 | 4.2 | 7.4 | 0.8 | 2.9 | 1.3 | 1.46 | 3.30 | 2.27 | 400.02 |
| Analysis #5 | 80.9 | 4.7 | 9.5 | 0.0 | 3.3 | 1.6 | 1.44 | 3.03 | 2.11 | 400.86 |
| Analysis #6 | 80.8 | 5.3 | 9.0 | 0.0 | 3.3 | 1.5 | 1.59 | 3.58 | 2.25 | 400.63 |
| Analysis #7 | 80.0 | 4.9 | 9.2 | 1.2 | 3.2 | 1.5 | 1.52 | 3.15 | 2.08 | 400.66 |
| Average | 81.2 | 4.8 | 8.9 | 0.5 | 3.2 | 1.5 | 1.52 | 3.27 | 2.15 | 400.53 |
| Std Dev | 1.6 | 0.8 | 0.9 | 0.5 | 0.5 | 0.3 | 0.09 | 0.17 | 0.11 | 0.35 |
| Poly(allyamine hydrochloride) | | | | | | | | | | |
| C3H8NCl (Theory) | 60.0 | 20.0 | | | 20.0 | | 1.0 | | | 401.06 |
| Based on N | 14.4 | 4.8 | | | 4.8 | | | | | |
| Based on Mn | | | 3.0 | | | 1.5 | | | | |
| Difference with Exp. | 66.8 | — | 5.9 | | −1.6 | — | | | | 0.53 |

Figure 1:
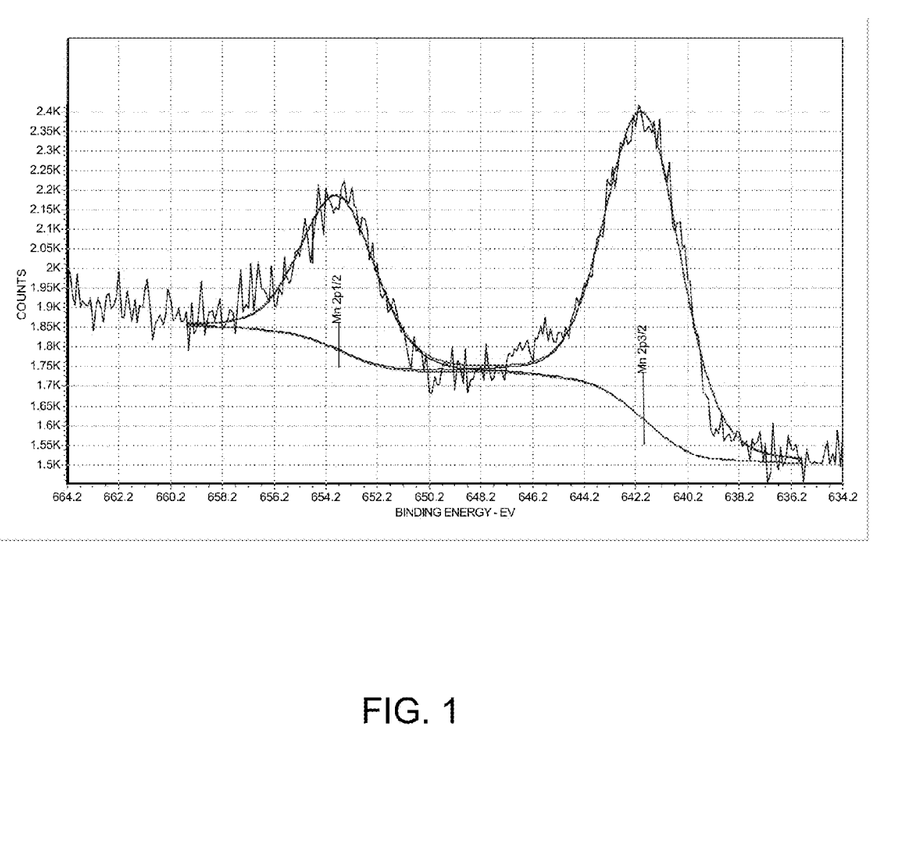
FIG. 1 shows a representative Mn2p curve-fit XPS spectrum from Analysis 5 of Table 2, with counts on the Y-axis and binding energy on the X-axis.

Seven high resolution scans (Analysis #1-7) of the Mn 2p region were performed. The results of the curve fitting analysis are shown in Table 2 and a representative Mn2p curve-fit XPS spectrum is shown in FIG. 1 with counts on the Y-axis and binding energy on the X-axis. From Table 2 it can be seen that:

The Binding Energy and Spin-orbit splitting (Delta) are consistent with manganese dioxide.

Figure 2:
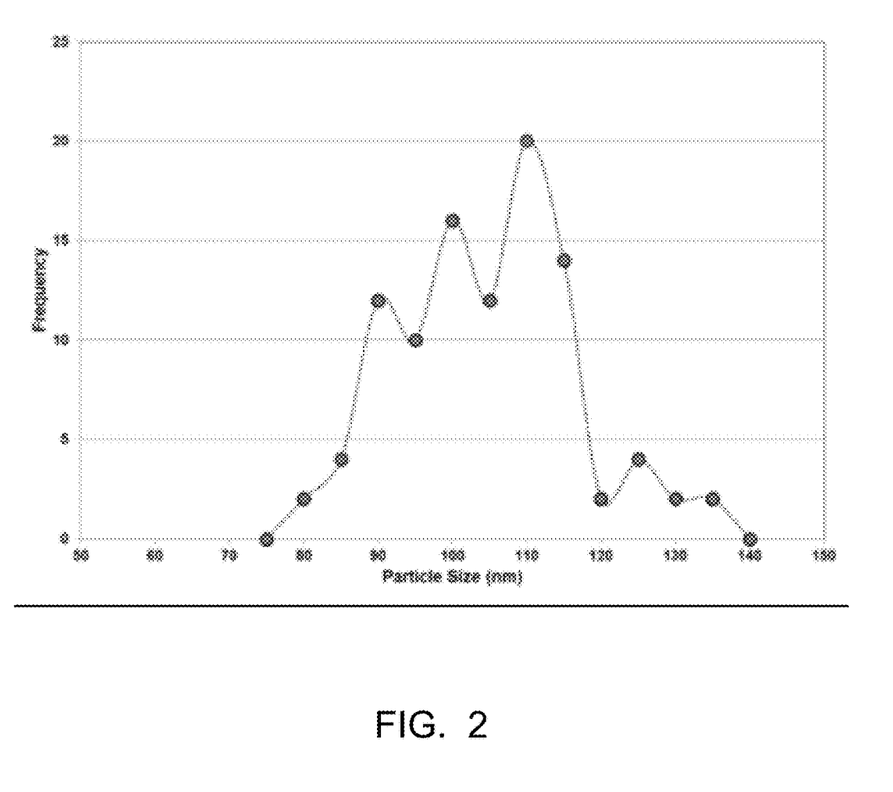
FIG. 2 is a graph of the TEM results that gave an average particle size of roughly 103 nm with particle size data listed in Table 3 with frequency on the Y-axis and particle size (nm) on the X-axis
Figure 3:
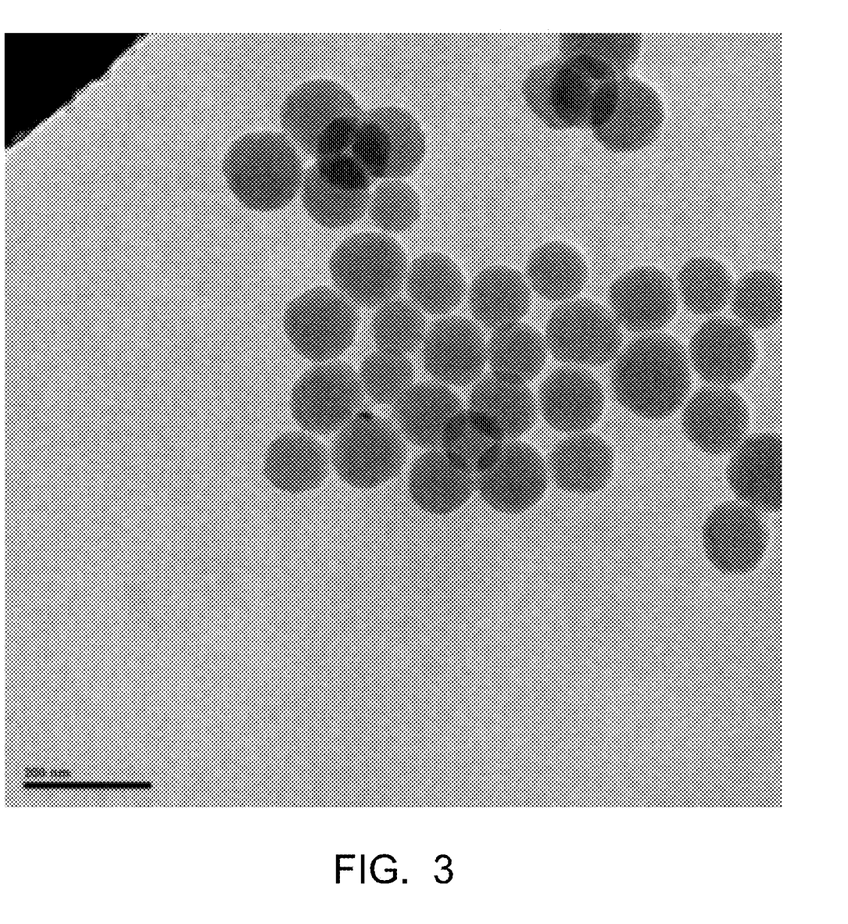
FIG. 3 represents the sample results from the Transmission electron microscopy (TEM) measurements showing the nanoparticles to be spherical in shape with an average diameter of individual nanoparticles of ~100 nm.

The peak area ratios are consistent with the expected ratio for 2p3/2 and 2p1/2.

quency on the Y-axis and particle size (nm) on the X-axis. Samples were prepared by capturing minute drops of the manganese dioxide nanoparticle solution on carbon coated/formvar grids as well as SiO2 coated grids to see if one sample had more particles present than the other. Both types of grids gave the same result. Some water was assumed to have evaporated in sample preparation for the TEM measurements (e.g. partial vacuum drying). Measurements were taken first with a standard to cross check calibration, and then the particles were measured using a nm scale. FIG. 3 represents the sample results from the TEM measurements.

TABLE 3

| manganese dioxide Nanoparticle data per TEM analysis | |
| --- | --- |
| Particle Count | 50 |
| Avg. (nm) | 102.6 |
| Std. Dev. (nm) | 11.7 |
| Max (nm) | 132 |
| Min (nm) | 79 |

Figure 4:
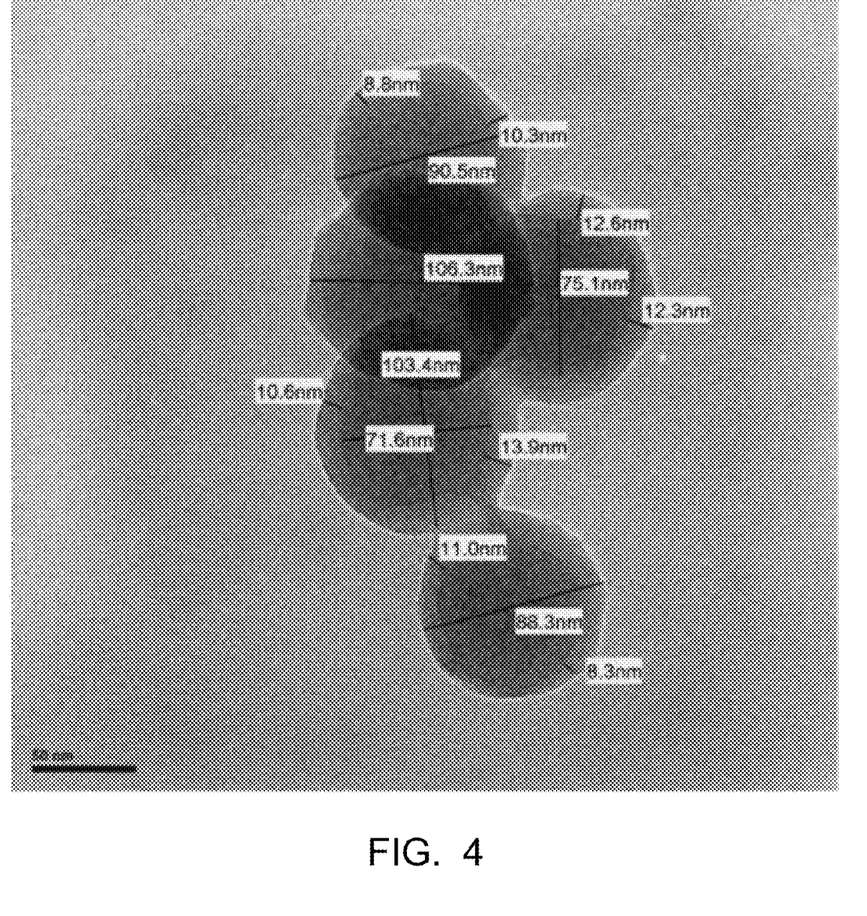
FIG. 4 is representative of high resolution TEM images that were taken in the sphere as well as around the sphere to see if there was a distinctive coating around the particles. Examination of these images revealed that the outer shell is roughly 8-12 nm in thickness.

High resolution TEM images were also taken in the sphere as well as around the sphere to see if there was a distinctive coating around the particles. FIG. 4 is representative of such high resolution TEM images. Examination of these images revealed that the outer shell is roughly 8-12 nm in thickness (as shown in FIG. 4).

Figure 5:
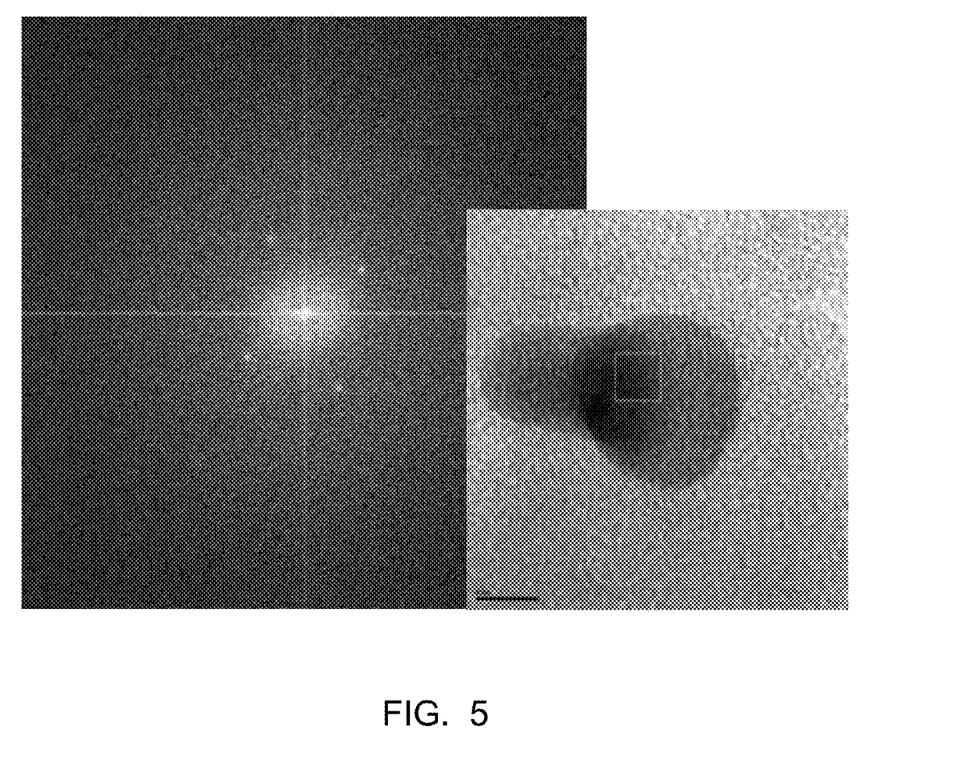
FIG. 5 shows a FFT analysis image with a crystal structure depiction (left) along with a TEM image (right) that identifies the location of the FFT analysis within the sphere as the central square.
Figure 6:
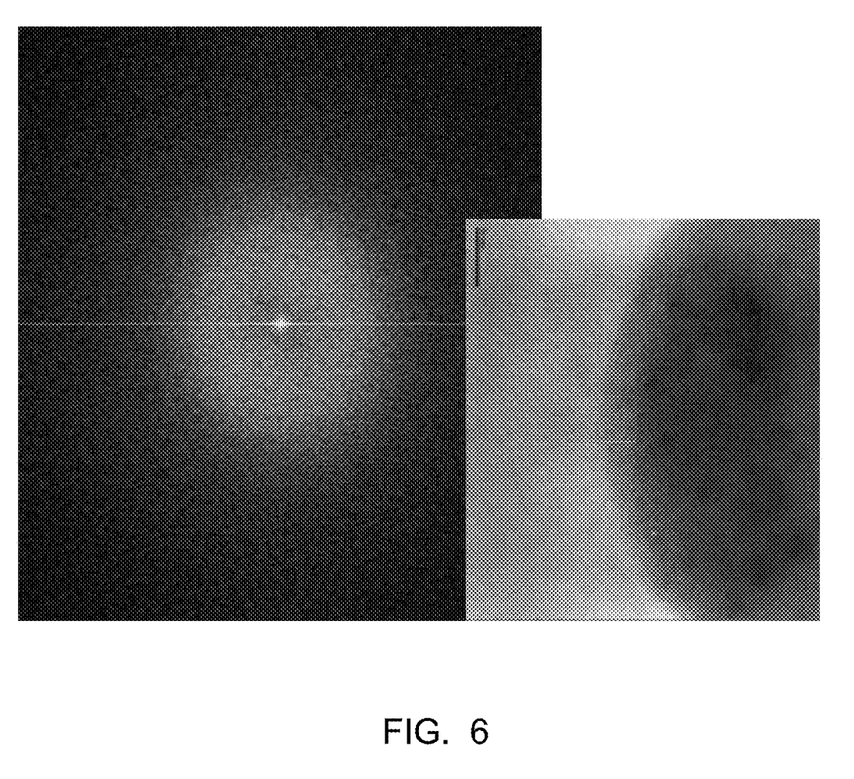
FIG. 6 shows a FFT analysis image with an amorphous structure depiction (left) along with a TEM image (right) that identifies the location of the FFT analysis within the sphere as the central square.

Additional support for the existence of a core/shell structure in the manganese dioxide nanoparticles is provided by Fast Fourier Transform (FFT) analysis images. Crystals were clearly detected within the spheres of individual nanoparticles, which is indicative of higher amounts of manganese dioxide in the core. FFT analysis images of the outer shell show the structure to be amorphous. This is interpreted to mean that there is a manganese dioxide core shielded by a PAH shell. FIG. 5 shows a FFT analysis image with a crystal structure depiction (left) along with a TEM image (right) that identifies the location of the FFT analysis within the sphere as the central square. FIG. 6 shows a FFT analysis image with an amorphous structure depiction (left) along with a TEM image (right) that identifies the location of the FFT analysis within the sphere as the central square.

Example 2

PVA Gel (Carrier for the Manganese Dioxide Nanoparticles)

(i) Stock Solutions Preparation

Four stock solutions were prepared as follows:
  PVOH stock solution=15 gram of Polyvinyl Alcohol (98-99% hydrolyzed, from Sigma-Aldrich) was dissolved in 85 gram of Di water in 80-90 degree Celsius to yield a 15% PVOH aqueous solution.
  Guar Gum stock solution=0.1 gram of Guar Gum (from Spectrum) dissolved in 9.9 mL of Di water for 1% Guar Gum aqueous solution.
  Gelatin stock solution=2 gram of Gelatin (Fish skin, from Sigma-Aldrich) was dissolved in 8 gram of Di water to make 20% Gelatin aqueous solution. 7.5% w/v sodium borate=7.5 gram of sodium borate (from Sigma-Aldrich) was dissolved in 100 mL of Di water in a glass bottle at 40-50 degree Celsius with a small magnetic stirrer. Note: this 7.5% w/v sodium borate solution was never made for more than 48 hours before use.

(ii) Preparation of PVA Gel 5 gram PVOH stock solution from above was mixed with 1.3 gram Guar gum stock solution in a 100 mL beaker, and then to this mix of solutions was added 0.5 gram glycerol (from WF Limited) to yield an intermediary mixture. To this intermediary mixture, 0.25 gram of 18% wt poly 4-styrenesulfonic acid aqueous solution (from Sigma-Aldrich) and 0.25 gram gelatin stock solution were then added in that order to give a viscous mixture. Finally to the viscous mixture, 1.5 mL of 7.5% w/v sodium borate was added and hand mixed vigorously with spatula to obtain a uniform gel. The addition of sodium borate initiates the crosslinking of borate anions with the hydroxyl groups of polyvinyl alcohol, thus yielding a cross-linked polymeric gel mass. During mixing, air bubbles were entrained into the gel mass that imparted initial opacity. However with time, the gel mass became colorless and transparent. The gel was stored in a small petri-dish that was sealed with Parafilm® sealant to prevent moisture loss.

Example 3

PVA Gel with Manganese Dioxide Nanoparticles

A viscous mass was prepared following the steps exactly as in Example 2 except the addition of gelatin stock solution was followed by the addition of 0.25 mL manganese oxide nanoparticles solution per Example 1. This caused the viscous mass to become light brown in color. After the final addition of 1.5 mL 7.5% w/v sodium borate, the viscous mass was mixed vigorously to polymerize into a gel with light brown tint. Air bubbles were temporarily entrapped in the gel mass during mixing, but these bubbles escaped from or dispersed in the gel mass to give a transparent gel. It was stored in a petri-dish per Example 2.

Example 4

PVA Gel with Colorant

For aesthetic purposes, a gel with color is preferred over colorless gel (Example 2). To add color to the gel, a blue food color (from McCormick Company) was used. Thus, a viscous mixture identical to that in Example 2(ii) was prepared except that before the addition of the 7.5% w/v sodium borate, a few drops of blue food color were added. The colorant was uniformly hand mixed into the viscous mixture. Finally 1.5 mL of 7.5% w/v sodium borate was added and mixed vigorously to yield blue colored PVA gel.

Example 5

PVA Gel as Reservoir for Dissolved Oxygen

PVA gel similar to Example 4 was made except that before the addition of sodium borate, 0.25 mL manganese oxide nanoparticles solution from Example 1 was added. After the addition of manganese dioxide, the color of the viscous mass changed from the original blue to teal. Finally (as before) 1.5 mL of 7.5% w/v sodium borate was added to initiate polymerization of the mass to a gel. The gel contained approximately 25 ppm of manganese dioxide.

To convert the gel into a reservoir of dissolved oxygen, 0.25 mL of 30% weight hydrogen peroxide aqueous solution (from Fisher Scientific) was hand-mixed in the gel vigorously. As the mixing of peroxide proceeded, its decomposition to yield oxygen as catalyzed by manganese dioxide was initiated. We unexpectedly observed that as the hydrogen peroxide decomposition proceeded, the teal color reverted back to the original blue color within less than 1-2 minutes. This color change was uniform throughout the gel mass. Due to the saturation of gel mass with dissolved oxygen, the excess oxygen bubbled out from the gel mass. As a result, the gel mass was filled with tiny oxygen bubbles imparting an opaque appearance. The opacity made the blue color slightly light, but as the bubbles escaped the gel regained its original blue shade. After the color change (back to the original blue), the gel mass was tested for peroxide content with the help of a test strip. The test read the presence of hydrogen peroxide of less than 10 ppm.

Example 6

Oxygen Flux Measurement from PVA Gel of Example 5

We corroborated the decomposition of hydrogen peroxide to oxygen in the gel of Example 5, as indicated by color change from teal to blue, by measuring oxygen flux at 25° C. from the gel mass. About 2.4 gm of freshly made PVA gel mass per Example 5, with some but not many entrapped air or oxygen bubbles, was transferred to a polyethylene (PE) membrane (~25 micron thick) of a Franz cell. The membrane acted as a flexible wall of the Franz cell that was filled with air saturated saline solution. The cell was fitted with a dissolved oxygen measuring probe (Foxy® probe from Ocean Optics, Fla.). The dissolved oxygen probe monitored the oxygen uptake by the saline solution in ppm over time. After this PVA gel was placed in contact with the PE membrane, the oxygen concentration in the saline was monitored. After an initial time lag of 5 minutes, the oxygen concentration began to increase linearly with time for the next 60 minutes. Using the linear slope value, the oxygen flux (in) was calculated as ~0.06 microgm/cm2/min.

Example 7

Oxygen Flux Measurement for Amigel® Gel

A gel stock was prepared by mixing 60 gram of Amigel® gel (from Alban Muller) with 540 gram of Di water in 90 degree Celsius to make a 10% wt. Amigel® aqueous solution. Amigel® gel is a natural polysaccharide with gelling and thickening properties; its uses include cosmetic formulations. Amigel® gel in aqueous solutions of from 0.8% concentration and greater form solid gels. This gel stock was used in the following two part gel preparation. As the first part, 0.6 mL of 30% wt hydrogen peroxide aqueous solution (from Fisher Scientific) was mixed with 30 gram of gel stock to yield approximately 0.6% hydrogen peroxide. As the second part, 10 mL of manganese dioxide nanoparticles solution (~900 ppm manganese dioxide) was mixed with 30 gram of gel stock solution to yield approximately 250 ppm manganese dioxide nanoparticles. 1.2 gram of the first part (0.6% hydrogen peroxide in gel stock) was mixed with 1.2 gram of the second part (250 ppm manganese dioxide nanoparticles in gel stock). The combined 2.4 gram mixed gel was transferred to a PE membrane of a Franz cell. The procedure to measure oxygen flux was repeated as in Example 6. The oxygen flux was measured to be ~0.2 microgm/cm$^2$/min.

The Franz Cell Chamber

The Franz Cell chamber is an in vitro skin permeation assay frequently used in formulation development. The Franz Cell apparatus consists of two primary chambers separated by a membrane. Although animal skin can be used as the membrane, human skin or other membranes such as the polyethylene used above are suitable. The test product is applied to the membrane via the top chamber. The bottom chamber contains fluid from which samples are taken at regular intervals for analysis. This testing determines the amount of active that has permeated the membrane at each time point. The chamber is maintained at a constant temperature. Depending on the vehicle, the rate of permeation as determined via Franz cell analysis can vary significantly (perhaps from 10- to 50-fold).

Example 8

Production of Manganese Oxide (MnO2) Nanoparticles Using PVP 2.22 g of Polyvinyl pyrrolidone (PVP, 40,000 MW Sigma-Aldrich, monomer FW: 111) was dissolved in 50 mL of de-ionized (Di) water to prepare 0.4M solution. 0.79 g of Potassium Permanganate (158.03 g/mol, Riedel-de-Haen) was dissolved in 50 mL of Di water to give 0.1M solution. Both solutions were mixed in a glass beaker (250 mL capacity) at room temperature with a magnetic stirrer for few minutes followed by drop-wise addition of 3.75 ml of 3% wt hydrogen peroxide. The peroxide addition caused effervescence and the solution color began to change to dark brown in 2-3 minutes, indicating the reduction reaction ($KMnO_4$ to $MnO_2$) took place. The UV-VIS spectrum of the final reacted mixed solutions was recorded and showed a peak at 320 nm consistent with absorption peak observed for manganese dioxide nanoparticle containing solution. The final reacted mixed solutions, equivalently termed manganese dioxide nanoparticle solution, had approximately ~4350 ppm manganese dioxide. The manganese dioxide nanoparticle solution was perceived as transparent (hence the use of the term solution rather than suspension). It was used immediately in the next step for making the polyacrylamide gel sheet.

Example 9

Production of Manganese Oxide (MnO2) Nanoparticles Using Triethanol Amine 0.149 g of reagent grade triethanolamine was dissolved in 50 mL of de-ionized (Di) water to prepare 0.02M solution. 0.158 g of Potassium Permanganate (158.03 g/mol, Riedel-de-Haen) was dissolved in 50 mL of Di water to give 0.02M solution. In a glass beaker (250 mL capacity) at room temperature with a magnetic stirrer containing triethanolamine solution, the KMnO4 solution was added drop-wise under stirring. The combined mixture looked brown soon after the first drop of permanganate solution was added. The UV-VIS spectrum of the final reacted mixed solutions was recorded and showed a peak at 300 nm consistent with absorption peak observed for manganese dioxide nanoparticle containing solution. The final reacted mixed solutions, equivalently termed manganese dioxide nanoparticle solution, had approximately ~900 ppm manganese dioxide. The manganese dioxide nanoparticle solution was perceived as transparent (hence the use of the term solution rather than suspension). It was immediately used in the next step for making the polyacrylamide gel sheet.

Example 10

Preparation of Polyacrylamide Hydrogel Sheet Containing MnO2 Nanoparticles Made Using PVP (Prophetic)

The recipe for preparing the hydrogel sheet on ~30 g scale is listed below. The recipe is somewhat similar to the recipe for making hydrogel sheet described in U.S. Pat. No. 5,196,190 and is slightly modified to suit the small scale preparation on the bench scale.

A. Monomer Solution

| | |
|---|---|
| DI water | 12.1 g |
| Methylenebisacrylamide | 0.018 g |
| Acrylamide | 1.482 g |
| Glycerol | 1.50 g | manganese dioxide solution from Ex. 8 1.25 g (to achieve MnO2~1000 ppm in dehydrated sheet)

B. Guar Gum Solution

| | |
|---|---|
| Guar gum | 0.165 g |
| Isopropanol | 0.75 g |
| DI water | 10 g |

C. TEMED Solution

| | |
|---|---|
| TEMED (tetramethyl ethylene diamine) | 0.0625 ml diluted with 1 ml DI water |
| Ammonium persulfate solution | 0.05 g dissolved in 1 ml DI water |

Procedure
1. In separate PP plastic cups (~150 ml capacity), prepared Solutions A and B respectively and set aside covered with lids. In preparing Solution B, transfer weighed quantity of dry guar gum powder to the cup and wet it with isopropanol thoroughly. Then add DI water in small aliquots (~1 ml) and hand-mix with a spatula breaking up any clumps. Continue adding water until the required amount is all used up to yield viscous solution. In preparing Solution A, dissolve all solid ingredients into DI water and finally add glycerol to obtain a clear solution. Pour slowly Solution A into Solution B (1-2 ml at a time) to obtain a uniform monomer solution.
2. In separate test tubes, prepare TEMED and APS solutions as indicated.
3. To the final monomer solution from (1), add TEMED solution and blend it in uniformly.
4. Finally, add freshly made APS solution to the solution in (3), mix it well and pour it a 4" dia PS petri-dish, cover it with lid and set aside for at least 1 h at room temperature to complete polymerization. The temperature may be raised to 45 C by placing the petri-dish in an oven pre-set to 45 C.
5. The polymerized gel sheet with amber color tint is carefully removed and placed on nylon mesh that is previously dabbed with a layer of mineral oil (this prevents the dehydrated sheet from sticking). The sheet is dehydrated for 3-4 h in an oven set at 55 C. This will yield a gel sheet with the consistency of fruit leather and can be handled without tacky feel. We have assumed that the dehydration will result in a gel sheet with the moisture content of ~10% wt of the final weight. With this assumption, the estimate of manganese dioxide nanoparticle solution to be added is made. We estimate the final concentration of manganese dioxide nanoparticle in dehydrated hydrogel sheet is ~1000 ppm.

The dehydrated gel sheet can be used in the preparing O2 containing sheet dressing.

Example 11

Polyacrylamide Hydrogel Sheet Containing Manganese Dioxide Nanoparticles Made Using Triethanol Amine (Prophetic)

The hydrogel sheet is made by following the recipe and the procedure of Example 10 except the amount of manganese dioxide nanoparticles solution used is from Example 9 and is estimated at 4 g. This corresponds to manganese dioxide content of the final dehydrated hydrogel sheet of ~1000 ppm. The light brown colored dehydrated gel sheet can be in the next step for preparing O2 containing foam dressing.

Example 12

Preparation of O2 Containing Foam Sheet Dressing Containing MnO2 Nanoparticles (Prophetic)

A small square piece (~1"×1") is cut from the dehydrated hydrogel sheet from Example 10 and placed in a 10% wt. solution of hydrogen peroxide for 5-10 minutes at ~25 C (the exact duration and peroxide concentration are not yet known). The peroxide solution penetrates the hydrogel sheet piece and hydrates it. The hydrated sheet is blotted dry on paper and transferred to a clean nylon mesh and placed inside an oven set to ~55 C for 1-2 hrs (the exact heating duration has not been determined). The exposure to higher than ambient temperature initiates rapid decomposition of hydrogen peroxide to oxygen gas throughout the gel sheet forming bubbles that are trapped within the gel sheet to produce a foam sheet dressing. The foam sheet dressing will have expanded and will be greater in size than the start gel sheet. The presence of manganese dioxide nanoparticle will provide catalytic effect to the decomposing peroxide and its uniform distribution within the gel sheet will ensure foaming reaction takes place evenly in the gel sheet. The foam sheet is tested for O2 flux measurement using the Franz cell experimental setup and is shown to deliver dissolved O2. The setup is described in another example in this disclosure.

While the disclosure has been described in detail with respect to specific embodiments thereof, it will be apparent to those skilled in the art that various alterations, modifications and other changes may be made to the disclosure without departing from the spirit and scope of the present disclosure. It is therefore intended that the claims cover all such modifications, alterations and other changes encompassed by the appended claims.

We claim:
1. A colorimetric indicator of peroxide decomposition to oxygen comprising a carrier and nanoparticle manganese dioxide having a UV-VIS spectrum of between about 300 and 350 nm prior to mixing with peroxide, a particle size of between 1 and 1000 nm, and a yellow-brown color, where, upon mixing of said carrier and nanoparticle manganese dioxide with peroxide, the yellow-brown color fades.
2. An on-demand oxygen generating topical composition comprising the colorimetric indicator of claim 1 specifically to indicate a color change (from colored to colorless) upon complete mixing of said indicator and an oxygen precursor.
3. The colorimetric indicator of peroxide decomposition to oxygen of claim 1 wherein said nanoparticle manganese dioxide carrier is a gel, foam or emulsion.

* * * * *